United States Patent
Sattler et al.

(10) Patent No.: US 9,968,272 B2
(45) Date of Patent: May 15, 2018

(54) DEVICE FOR DETECTING ELECTRIC POTENTIALS

(71) Applicant: Drägerwerk AG & Co. KGaA, Lübeck (DE)

(72) Inventors: Frank Sattler, Lübeck (DE); Marcus Eger, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 0 days. days.

(21) Appl. No.: 14/923,859

(22) Filed: Oct. 27, 2015

(65) Prior Publication Data

US 2016/0113532 A1  Apr. 28, 2016

(30) Foreign Application Priority Data

Oct. 28, 2014  (DE) .................. 10 2014 015 896

(51) Int. Cl.
*A61B 5/05* (2006.01)
*A61B 5/04* (2006.01)

(52) U.S. Cl.
CPC .................. *A61B 5/04004* (2013.01)

(58) Field of Classification Search
CPC ........ A61B 5/0215; A61B 5/0531; A61B 5/08
USPC .......................... 600/300, 372, 547; 128/709
See application file for complete search history.

(56) References Cited

U.S. PATENT DOCUMENTS

| | | | | |
|---|---|---|---|---|
| 4,416,288 A | * | 11/1983 | Freeman | A61B 5/0476 600/544 |
| 4,448,202 A | * | 5/1984 | Wajszczuk | A61B 5/04004 600/522 |
| 4,548,204 A | * | 10/1985 | Groch | A61B 5/024 128/904 |
| 5,269,325 A | * | 12/1993 | Robinson | A61B 5/04005 324/248 |

(Continued)

FOREIGN PATENT DOCUMENTS

| | | |
|---|---|---|
| DE | 29 26 165 A1 | 1/1980 |
| DE | 10 2007 046 510 A1 | 4/2009 |
| WO | 2009/017413 A1 | 2/2009 |

OTHER PUBLICATIONS

Bruce B. Winter et al., Driven-Right-Leg Circuit Design, IEEE Transactions on Biomedical Engineering, vol. BME-30, No. 1, Jan. 1983.

*Primary Examiner* — May Abouelela
(74) *Attorney, Agent, or Firm* — McGlew and Tuttle, P.C.

(57) ABSTRACT

A device detects electric potentials with measuring inputs (7) for connection to measuring electrodes (9), which can be placed on the body of a patient (3). Measuring amplifiers ($Op_1, \ldots, Op_N$) have a first and a second input as well as an output (11). A summing unit (13, 23) is connected to the outputs of the measuring amplifiers and sends a signal proportional to a mean value of the signals of the outputs of the measuring amplifiers to an output (15, 17) of the summing unit. Each of the measuring inputs is connected to a first input of a measuring amplifier. The second input of (Continued)

each measuring amplifier is connected to the output (17) of the summing unit. A potential output (19) connects to an electrode and to an output of a further amplifier $Op_c$), with an input connected to the output (15) of the summing unit.

13 Claims, 2 Drawing Sheets

(56) References Cited

U.S. PATENT DOCUMENTS

| | | | | |
|---|---|---|---|---|
| 5,678,547 | A * | 10/1997 | Faupel | A61B 5/04 600/409 |
| 5,687,724 | A * | 11/1997 | Jewett | G06K 9/0057 324/244 |
| 6,351,666 | B1 * | 2/2002 | Cuzick | A61B 5/04 128/920 |
| 6,633,777 | B2 * | 10/2003 | Szopinski | A61B 5/0532 324/692 |
| 8,594,764 | B2 * | 11/2013 | Rice | A61B 5/04 381/56 |
| 2002/0183635 | A1 * | 12/2002 | Yonce | A61B 5/0428 600/509 |
| 2003/0083584 | A1 * | 5/2003 | Yonce | A61B 5/0424 600/509 |
| 2005/0010265 | A1 * | 1/2005 | Baru Fassio | A61B 5/112 607/48 |
| 2009/0088654 | A1 * | 4/2009 | Demharter | A61B 5/0428 600/509 |
| 2011/0201936 | A1 * | 8/2011 | Miyajima | G01S 7/52023 600/459 |
| 2011/0208028 | A1 * | 8/2011 | Rossi | A61B 5/0537 600/372 |
| 2012/0190985 | A1 * | 7/2012 | Hisatsu | A61B 8/5269 600/459 |
| 2013/0267816 | A1 * | 10/2013 | Eder | A61B 5/04001 600/377 |
| 2015/0108328 | A1 * | 4/2015 | Guo | H04N 5/361 250/208.1 |
| 2015/0263673 | A1 * | 9/2015 | Biel | A61B 5/04 600/372 |
| 2016/0089084 | A1 * | 3/2016 | Sugiyama | B60N 2/002 600/372 |

* cited by examiner

DEVICE FOR DETECTING ELECTRIC POTENTIALS

CROSS REFERENCE TO RELATED APPLICATIONS

This application claims the benefit of priority under 35 U.S.C. § 119 of German Patent Application 10 2014 015 896.9 filed Oct. 28, 2014, the entire contents of which are incorporated herein by reference.

FIELD OF THE INVENTION

The present invention pertains to a device for detecting electric potentials, for example, of the body of a patient, with a plurality of measuring inputs for connecting to measuring electrodes which can be placed on the body of a patient, with a plurality of measuring amplifiers, which have a first and a second input as well as an output, and with a summing unit, which is connected to the outputs of the measuring amplifiers and which is designed to send a signal proportional to the mean value of the signals of the outputs of the measuring amplifiers to an output of the summing unit, wherein each of the measuring inputs is connected to a first input of a measuring amplifier and wherein the second input of each measuring amplifier is connected to the output of the summing unit. Further, the present invention pertains to a method for detecting electric potentials.

BACKGROUND OF THE INVENTION

When measuring electric potentials, for example, on the skin of a patient, the useful signal contained in these potentials lies only in the mV range, as may be the case in an electrocardiogram (ECG), an electromyogram (EMG), an electroencephalography (EEG) or an electrooculography (EOG). As such the following problems arise.

Since the body of the patient is surrounded by electric fields, potentials are formed due to capacitive coupling on the skin of the patient. This effect can generally be described in such a way that the body is coupled capacitively especially to a 230V/50 Hz alternating voltage field which is caused by power supply sources located in the surrounding area of the patient. For the sake of safety, it is, however, not allowable to couple the patient directly to a uniform surrounding ground, because this would cause a considerable risk to the patient.

In addition, likewise for the sake of safety, a measuring device, to which the electrodes on the skin of the patient are connected, must also be galvanically separated from a surrounding ground. This in turn implies that the measuring device is also coupled with its internal ground capactively to the surrounding area, so that the problem arises that the device ground lies at a potential, whose level is not known, and which generally differs from the potential of the patient.

In order to at least achieve that the patient and the ground of the measuring device lie on the same potential or at least that there be a fixed potential difference present between both, it is known to connect the device ground and the body of the patient to one another via an additional electrode.

Since, however, the device ground and the patient may generally lie on a different potential because of the inhomogeneity of the surrounding fields, which arises from the different capacitive coupling to the surrounding area, an equalizing current flows. This leads to a so-called common mode signal because of the impedance of the coupling to the patient via the electrodes, which is amplified by the amplifiers in the measuring device. When the useful signals, actually to be detected with the measurement, are very small, the common mode signal leads to the actual useful signal no longer being able to be resolved. Moreover, the difficulty arises that the amplifiers must have a high input dynamic range, so that the useful signal and the higher common mode signal overlaying this can be processed. Furthermore, a digital electronic analyzing unit arranged downstream must have a high number of bits per measured value to be able to process the large signals.

For this purpose, it is known from Bruce B. Winter et al., Driven-Right-Leg Circuit Design, IEEE Transactions on Biomedical Engineering, Vol. BME-30, No. 1, January 1983, to apply a potential, which corresponds to the mean value of the signals detected at the measuring electrodes, wherein this mean value signal is also amplified, to the additional electrode arranged on the patient by the measuring device. In order to suppress the common mode signal significantly in this way, high amplifications are necessary for the mean value signal, which is difficult to achieve. In particular, the problem arises that oscillations in the outputted signal occur in high level amplifications.

In addition, it is, further, known from DE 29 26 165 A1, on which the present invention is based, to subtract the mean value of the signals, which are sent by the amplifiers, from the input signals of the amplifiers. However, the problem here is that the common mode signal is not amplified, but rather is sent together with the useful signal at the output of the amplifier. When the useful signal is extremely small, this may cause the level of the common mode signal and that of the amplified useful signal to be on the same order of magnitude, so that these cannot easily be separated from each other. In addition, there is the problem that the amplifiers and an electronic analyzing unit arranged downstream must be adapted to also further process the comparatively large common mode signal.

SUMMARY OF THE INVENTION

Based upon this, an object of the present invention is to design a measuring device for detecting potentials in such a way that common mode signals are reliably removed from the signal.

This object is accomplished by the device having a potential output for connecting to an electrode, which can be placed on the body of the patient, and by a first amplifier (further amplifier) being provided, whose input is connected to the output of the summing unit and whose output is connected to the potential output.

Thus, in the device according to the present invention, the mean value signal, which is sent from the summing unit, is fed back to the second input of each measuring amplifier, on the one hand, and subtracted there from the directly detected input signal, as a result of which a first reduction of the common mode signal offset is achieved in the output signal sent to the measuring amplifiers. On the other hand, the mean value signal is fed to a first amplifier, whose output is in turn connected to the potential output, which is connected to an additional electrode on the patient. In this connection, the mean value signal is amplified, which likewise has the effect that the common mode signal is further reduced in the output signal at the outputs of the measuring amplifiers.

Due to the combination of these two principles, a considerable reduction of the common mode signal offset can be achieved without it being necessary in this connection to provide a level amplification in the branch between the summing unit and the potential output, to which the additional electrode is connected.

When the mean value signal is sent to the additional electrode in an unamplified form, there is already a reduction or suppression of the common mode signal, which is twice as large as in the case when it is processed without the first amplifier and the additional electrode. When a moderate amplification of 10 is selected for the first amplifier, the common mode signal is suppressed more strongly with a factor 11 than in the case when the first amplifier is dispensed with. Thus, a considerable effect can already be achieved with slight amplifications in the branch to the additional electrode. In addition, it is achieved that the common mode signal is overall smaller and the input voltage range of the measuring amplifiers is not exceeded. This may otherwise easily happen when the mean value signal is only coupled back to the inputs of the measuring amplifiers. As will still be described in detail in connection with the preferred exemplary embodiments, this effect results from the interaction of the feeding back of the mean value signal to the second inputs of the measuring amplifiers and of the feeding of the mean value signal in amplified form to the additional electrode.

In a preferred embodiment, the summing unit comprises a microprocessor unit that is configured by program implementation to send to a first output a signal, whose level corresponds to the mean value of the signals of the outputs of the measuring amplifiers, wherein the input of the first amplifier is connected to this first output of the microprocessor unit.

It is further preferred in this connection when the microprocessor unit also has a second output, to which a signal is likewise sent, whose level corresponds to the mean value of the signals of the outputs of the measuring amplifiers, wherein this signal is amplified by a factor V. The second inputs of the measuring amplifiers are connected to this second output of the microprocessor unit, so that the suppression of the common mode signal can be further adapted via the selection of the amplification V.

Finally, the summing unit may also be embodied by means of an analog technique by having a second amplifier, one input of which is connected to the outputs of the measuring amplifiers such that a signal, whose level corresponds to the mean value of the signals of the outputs of the measuring amplifiers, i.e., is equal to the mean value or at least proportional thereto, is sent to the output of the second amplifier. Here, it is clear for the person skilled in the art how to achieve such a mean value circuit by using analog technique with an amplifier or operational amplifier. In addition, the output of this second amplifier is then connected to the second inputs of the measuring amplifiers and to the input of the first amplifier, wherein the latter can then in turn be connected to the additional electrode on the patient.

According to a second aspect of the present invention, the above-mentioned object is accomplished by a method for detecting electric potentials, wherein the potentials are detected as input signals, each one being fed to a first input of a plurality of measuring amplifiers and amplified to output signals, wherein a mean value signal of the output signals is formed, whose level is proportional to the mean value of the output signals, wherein the mean value signal is fed to second inputs of the measuring amplifiers and wherein the mean value signal is fed to a potential output, which is connected to an additional electrode. The advantages already explained in connection with the device according to the present invention are associated with this method.

The present invention is explained below based on a drawing showing only preferred exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
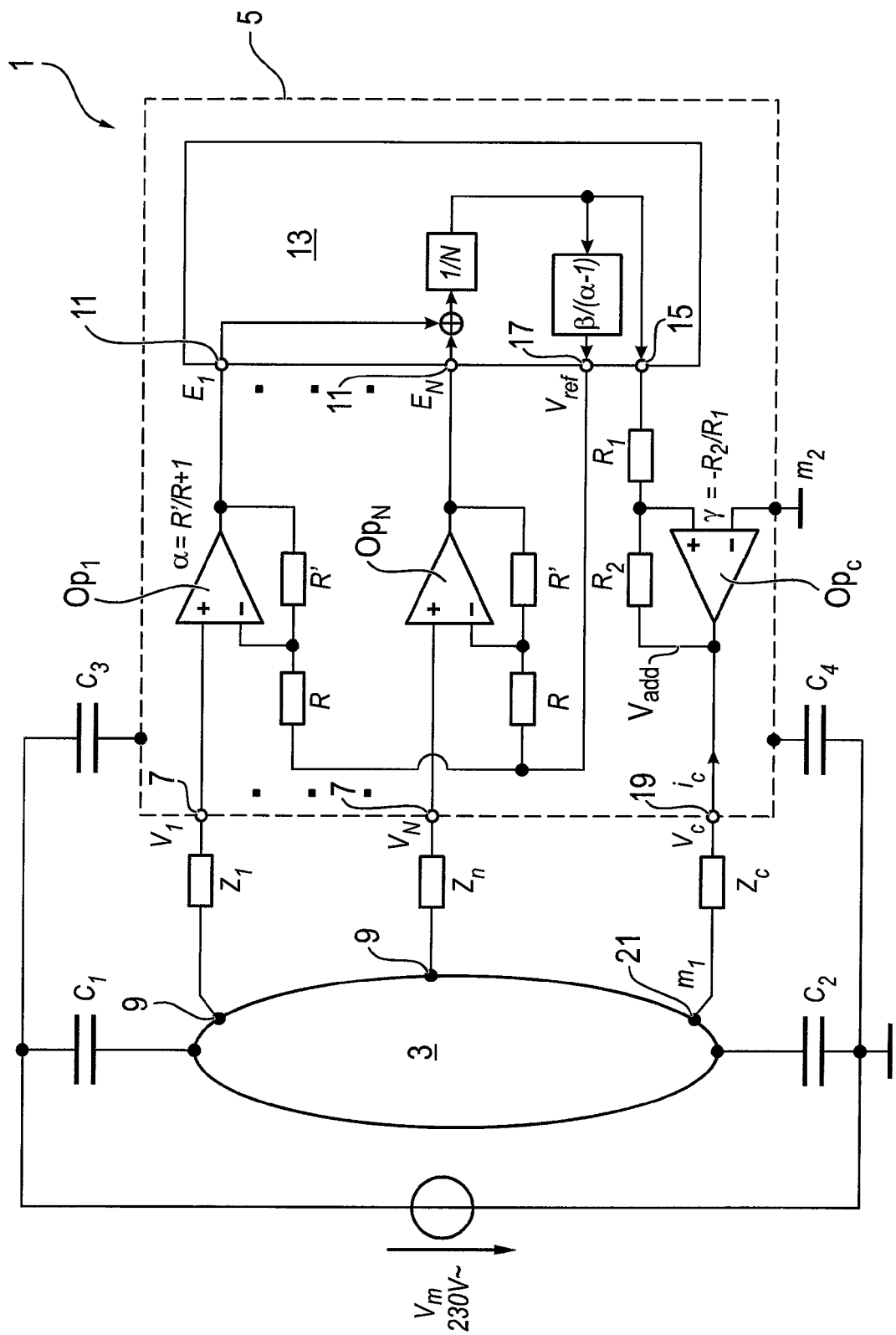
FIG. 1 is a schematic view of a first exemplary embodiment of a device according to the present invention for detecting potentials.

Referring to the drawings, FIG. 1 shows a view of the first exemplary embodiment of a device 1 according to the present invention for detecting potentials. In this case potentials are measured on the skin of a patient 3 (only shown schematically). It is first suggested, considering the capacities $C_1, C_2, C_3$ and $C_4$, that both the patient 3 and the housing 5, which forms the ground $m_2$ of the device 1, be coupled capacitively to the surrounding area and especially to a 50 Hz alternate voltage field. The result of this field is that the patient 3, on the one hand, and the housing 5 or the device ground $m_2$ of the device 1 connected to it, on the other hand, may have a different potential.

The device 1 has a plurality of measuring inputs 7, at which input signals $V_1, \ldots, V_N$ can be detected, wherein the measuring inputs 7 can be connected to electrodes 9 on the skin of the patient 3 and the connection between the measuring inputs 7 and the skin of the patient 3 has an impedance $Z_1, \ldots, Z_N$.

The device 1 has, furthermore, a number of measuring amplifiers $Op_1, \ldots, Op_N$ corresponding to the number of measuring inputs 7, whose first, non-inverting input is always connected to a measuring input 7. The outputs 11 of the measuring amplifiers $Op_1, \ldots, Op_N$ are used, on the one hand, to pick off the respective output signal $E_i$ amplified thereon compared to the input signal $V_i$, which is an indicator of the course over time of the potential on the skin of the patient 3. On the other hand, the outputs 11 are connected to a summing unit, which is designed as a microprocessor unit 13 in this first preferred exemplary embodiment.

The microprocessor unit 13 is configured by program implementation such that the microprocessor unit 13 generates, from the output signals $E_1, \ldots, E_N$ sent to the outputs 11, a mean value signal, with a signal level that corresponds to the mean value of the signals $E_i$ sent to the outputs 11. This mean value signal is, on the one hand, sent from the microprocessor unit 13 to a first output 15, and, on the other hand, the mean value signal, optionally amplified by a factor $V=\beta/(\alpha-1)$, is sent to a second output 17.

The first output 15 of microprocessor unit 13 is connected to the inverting input of a first amplifier (further amplifier) $Op_c$, whose non-inverting input is connected to the device ground $m_2$ of the device 1. The first amplifier $Op_c$ is thus connected as an inverting amplifier, and the amplification $\gamma$ can be adjusted via the resistances $R_1$ and $R_2$, with which the mean value signal is sent as an amplified reference signal $V_c$ to a potential output 19 of the device 1, to which the output of the first amplifier $Op_c$ is connected. The first amplifier $Op_c$ may also be connected as a non-inverting amplifier. However, the signal fed to this further amplifier $Op_c$ from the microprocessor unit 13 would then have to be inverted beforehand. The potential output 19 is connected to the additional electrode 21 on the patient 3.

The second output 17 of the microprocessor unit 13 is connected via the resistances R to the second, inverting input of the measuring amplifiers $Op_1, \ldots, Op_N$, so that the optionally amplified mean value signal is subtracted from the input signal $V_1, \ldots, V_N$, which is detected by the measuring inputs 7.

This first preferred exemplary embodiment works as follows.

Since the measuring amplifiers $Op_1, \ldots, O_N$ are connected as non-inverting amplifiers, the input signal $V_1, \ldots, V_N$ detected at the measuring inputs 7 amplified by a factor $$\alpha = 1 + \frac{R'}{R}$$

is sent to the outputs 11 of the measuring amplifiers $Op_1, \ldots, Op_N$.

The mean value signal $\overline{E}_i$, which is amplified in this connection, however, by a factor $\alpha-1$, is subtracted from this, however. Thus, the following arises for the output signal $E_1, \ldots, E_N$ at the output 11 of the measuring amplifiers $Op_1, \ldots, Op_N$:

$$E_i = \alpha \cdot V_i - \frac{\beta}{\alpha - 1} \cdot (\alpha - 1) \cdot \overline{E}_i.$$

When the mean value $\overline{E}_i$ for the output signals $E_i$ formed, the following equation arises for this:

$$\overline{E}_i = \alpha \cdot \overline{V}_i - \beta \cdot \overline{E}_i$$

Since the mean $\overline{V}_i$ corresponds to the common mode signal $V_{cm}$, the result is $$\overline{E}_i = \frac{\alpha}{1+\beta} \cdot V_{cm}.$$

Since the signal at the measuring inputs 7 is composed of the actual signal $\hat{V}_1$ and the common mode offset $V_{cm}$, the first equation can also be written as $$E_i = \alpha \cdot (\hat{V}_i + V_{cm}) - \beta \cdot \frac{\alpha}{1+\beta} \cdot V_{cm}.$$

or $$E_i = \alpha \cdot \hat{V}_i + \frac{\alpha}{1+\beta} \cdot V_{cm}.$$

The result of the last equation is that the difference between two input signals $V_i$ at the outputs 11 of the measuring amplifiers $Op_1, \ldots, Op_N$ is amplified by the factor $|A_{diff}|=\alpha$, while the common mode signal is amplified by the factor $|A_{gleich}|=\alpha/(1+\beta)$.

For the common mode suppression $CMRR=|A_{diff}|/|A_{gleich}|$, $CMRR=(1+\beta)$. Because of the difference formation and inaccuracies in the resistances R, R', an additional factor $CMRR_{diff}$ is also present, so that the equation $CMRR_{ges}=(1+\beta) \cdot CMRR_{diff}$ is obtained overall for the common mode suppression.

These considerations apply without it being taken into consideration that the mean value signal $\overline{E}_1$ amplified by the amplification $\gamma$ is in contact with the patient via the additional electrode 21. This leads overall to a damping of the common mode offset, so that $$V_{cm,ges} = V_{cm} \cdot \frac{1}{1+G}$$

and $$G = \gamma \cdot \frac{\alpha}{1+\beta}$$

then applies for the common mode offset $V_{cm, ges}$, which is then to be used in the previous equations.

The equation $$CMRR'_{ges} = CMRR_{ges} \cdot (1+g) = CMRR_{diff} \cdot (1+\beta) \cdot \left(1 + \gamma \cdot \frac{\alpha}{1+\beta}\right)$$
$$= CMRR_{diff} \cdot (1+\beta+\gamma\alpha).$$

is then obtained for the entire common mode suppression $CMRR'_{ges}$.

When the amplifications at the measuring amplifiers $Op_1, \ldots, Op_N$ as well as for the mean value signal fed to the second, inverting inputs of the measuring amplifiers $Op_1, \ldots, Op_N$ are selected in such a way that $\beta=\alpha-1$, this equation is further simplified to $CMRR'_{ges}=CMRR_{diff} \cdot \alpha \cdot (1+\gamma)$ This means that the common mode suppression is doubled already when the mean value signal of the additional electrode 21 is fed back in an unamplified form, i.e., $\gamma=1$. An amplification of the mean value signal by the factor 10, i.e., $\gamma=10$, leads to an increase in the common mode suppression by the factor 11.

This shows that due to the design according to the present invention or the combination of the feeding back of the mean value signal to the second, here inverting, input of the measuring amplifiers $Op_1, \ldots, Op_N$ as well as the feeding of the mean value signal to an additional electrode 21, the common mode signal can be strongly suppressed, without high amplifications being necessary for this. This stems directly from a combination effect of both feedbacks, and does not result independently of one another, as the previous considerations show.

Figure 2:
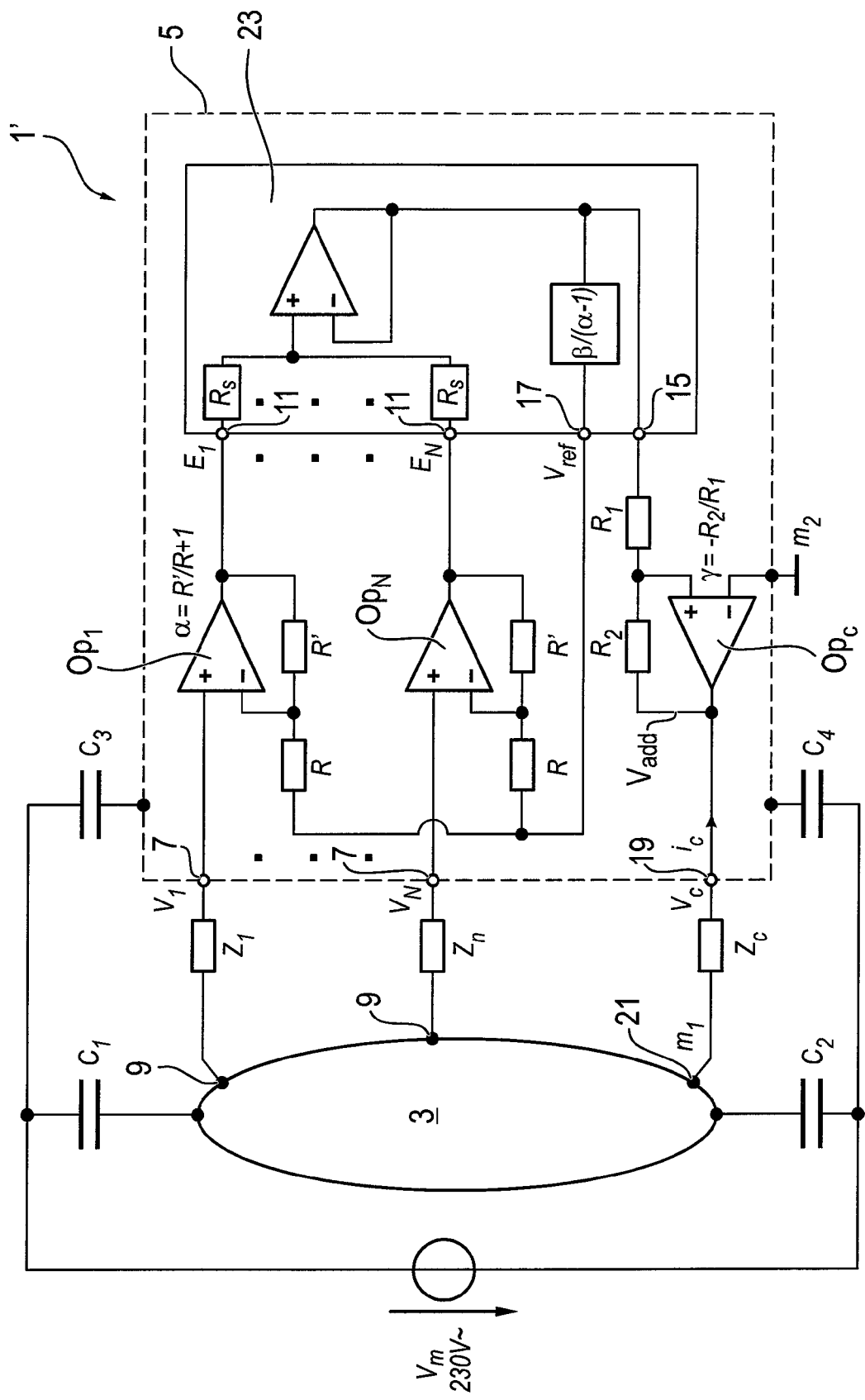
FIG. 2 is a schematic view of a second exemplary embodiment of a device according to the present invention for detecting potentials.

The second exemplary embodiment of a device 1' according to the present invention for detecting potentials, shown in FIG. 2, differs from the first exemplary embodiment only in that the summing unit is not designed as a microprocessor unit, but rather comprises a second amplifier (summing unit amplifier) 23, which is connected as a non-inverting amplifier that has an output provided with a mean value signal, having a signal level that corresponds to the mean value of the output signals $E_1, \ldots, E_N$ sent to the outputs 11 of the measuring amplifiers $Op_1, \ldots, Op_N$. This mean value signal is fed, optionally in an amplified form, on the one hand, as also in the first exemplary embodiment, to the second inverting inputs of the measuring amplifiers $Op_1, \ldots, Op_N$. On the other hand, this mean value signal is in turn fed to the first amplifier $Op_c$ and is guided in amplified form to the potential output 19 and fed to the additional electrode 21.

Thus, in this device 1' as well, potentials are detected at the measuring electrodes 7 as input signals $V_1, \ldots, V_N$, fed to the measuring amplifiers $Op_1, \ldots, Op_N$, where they are amplified to output signals $E_1, \ldots, E_N$, and a mean value signal of these output signals $E_1, \ldots, E_N$ is formed. This mean value signal is then in turn fed to the inputs of the measuring amplifiers $Op_1, \ldots, O_N$ as well as to the first amplifier $Op_c$. Thus, the advantages explained in connection with the first exemplary embodiment are achieved here as well. According to this second embodiment only the summing unit has an analog design by means of an amplifier 23 and not a digital design, as with the first exemplary embodiment, by means of a microprocessor unit 13.

While specific embodiments of the invention have been shown and described in detail to illustrate the application of the principles of the invention, it will be understood that the invention may be embodied otherwise without departing from such principles.

LIST OF REFERENCE NUMBERS 1, 1' Device
3 Patient
5 Housing
7 Measuring input
9 Electrode
11 Output—Measuring amplifier
13 Microprocessor unit
15 First output—Microprocessor unit
17 Second output—Microprocessor unit
19 Potential output
21 Additional electrode
23 Second amplifier
$V_i$ Input signal
$E_i$ Output signal
$Op_i$ Measuring amplifier
$Op_c$ First amplifier

What is claimed is:

1. A device for detecting electric potentials of electrodes configured to be placed on a body of a patient in cooperation with an additional electrode configured to be placed on the body of the patient, the device comprising: a plurality of measuring electrode inputs;
a plurality of measuring amplifiers, each of the plurality of measuring amplifiers comprising a first measuring amplifier input and a second measuring amplifier input and a measuring amplifier output;
a summing unit with summing unit inputs each of the summing unit inputs being connected to a respective one of the measuring amplifier outputs of the measuring amplifiers, the summing unit being configured to send a signal, proportional to a mean value of signals of the measuring amplifier outputs of the measuring amplifiers, to a summing unit output, wherein:
each of the measuring electrode inputs is connected to the first measuring amplifier input of a respective one of the measuring amplifiers; and the summing unit output of the summing unit is connected to each second measuring amplifier input of the measuring amplifiers; an additional electrode potential output; and
a further amplifier with a further amplifier input connected to the summing unit output of the summing unit and with a further amplifier output connected to the additional electrode potential output.

2. A device in accordance with claim 1, wherein:
the summing unit comprises a microprocessor unit which is configured by program implementation to send the signal to an output of the microprocessor unit, the output of the microprocessor unit forming at least a portion of the summing unit output, with the signal having a signal level that corresponds to the mean value of the signals of the outputs of the measuring amplifiers; and
the input of the further amplifier is connected to said output of the microprocessor unit.

3. A device in accordance with claim 2, wherein:
the microprocessor unit is further configured to send a further signal to a further output of the microprocessor unit, the further output of the microprocessor unit forming at least another portion of the summing unit output;
the further signal having the signal level corresponding to the mean value of the signals of the outputs of the measuring amplifiers amplified by a factor; and
the further output of the microprocessor unit is connected to the second inputs of the measuring amplifiers.

4. A device in accordance with claim 1, wherein: the summing unit comprises a summing unit amplifier with one input connected to the outputs of the measuring amplifiers such that the signal is sent to an output of the summing unit amplifier with a signal level that corresponds to the mean value of the signals of the outputs of the measuring amplifiers; and
the output of the summing unit amplifier is connected to the second inputs of the measuring amplifiers and to the input of the further amplifier.

5. A method for detecting electric potentials for connected measuring electrodes, which electrodes configured to be placed on a body of a patient, the method comprising the steps of:
providing a plurality of measuring electrode measuring inputs;
providing a plurality of measuring amplifiers with each of the plurality of amplifiers
comprising a first measuring amplifier input and a second measuring amplifier input and a measuring amplifier output;
feeding an input signal, from each of the plurality of measuring inputs, to the first input of a corresponding one of the plurality of measuring amplifiers;
amplifying the fed input signals to provide output signals at each of the plurality of measuring amplifiers;
providing an additional electrode potential output;
providing a summing unit with summing unit inputs respectively connected to the outputs of the measuring amplifiers, the summing unit being configured to send a signal, proportional to a mean value of the signals of the outputs of the measuring amplifiers, to a summing unit output, wherein:
each of the measuring inputs is connected to the first input of a respective one of the measuring amplifiers;
the output of the summing unit is connected to each second input of the measuring amplifiers; and providing a further amplifier with a further amplifier input connected to the output of the summing unit and with a further amplifier output connected to the additional electrode potential output.

6. A method in accordance with claim 5, wherein: the summing unit comprises a microprocessor unit which is configured by program implementation to send the signal to an output of the microprocessor unit, the output of the microprocessor unit forming at least a portion of the summing unit output, with the signal having a signal level that corresponds to the mean value of the signals of the outputs of the measuring amplifiers; and the input of the further amplifier is connected to said output of the microprocessor unit.

7. A method in accordance with claim 6, wherein: the microprocessor unit is further configured to send a further signal to a further output of the microprocessor unit, the further output of the microprocessor unit forming at least another portion of the summing unit output;
the further signal has the signal level corresponding to the mean value of the signals of the outputs of the measuring amplifiers amplified by a factor; and the further output of the microprocessor unit is connected to the second inputs of the measuring amplifiers.

8. A method in accordance with claim 6, wherein:
the summing unit comprises a summing unit amplifier with one input connected to the outputs of the measuring amplifiers such that the signal is sent to an output of the summing unit amplifier with a signal level that corresponds to the mean value of the signals of the outputs of the measuring amplifiers; and
the output of the summing unit amplifier is connected to the second inputs of the measuring amplifiers and to the input of the further amplifier.

9. A method in accordance with claim 6, further comprising:
providing a plurality of measuring electrodes;
connecting each measuring electrode to a respective one of the plurality of measuring electrode measuring inputs;
providing an additional electrode; and
connecting the additional electrode to the additional electrode potential output.

10. A device for detecting electric potentials of electrodes configured to be placed on a body of a patient in cooperation with an additional electrode configured to be placed on the body of the patient to apply an additional electrode signal to the patient for reducing a common mode signal, the device comprising:
a plurality of measuring electrode inputs;
at least one additional signal electrode output;
a plurality of measuring amplifiers, each of the measuring amplifiers comprising a first measuring amplifier input and a second measuring amplifier input and a measuring amplifier output;
a summing unit with summing unit inputs, each of the summing unit inputs being connected to a respective one of the measuring amplifier outputs of the measuring amplifiers, the summing unit being configured to send a signal, proportional to a mean value of the signals of the outputs of the measuring amplifiers, to a summing unit output, wherein:
each of the plurality of measuring amplifiers is associated with one of the plurality of measuring electrode inputs with each of the measuring electrode inputs connected to the first input of the associated one of the measuring amplifiers and providing an amplified measurement output associated with said one of the plurality of measuring electrode inputs; and
the summing unit output of the summing unit is connected to each second input of the measuring amplifiers; an electrode potential output; and
a further amplifier with a further amplifier input connected to the output of the summing unit and with a further amplifier output connected to the electrode potential output.

11. A device in accordance with claim 10, wherein:
the summing unit comprises a microprocessor unit which is configured by program implementation to send the signal to an output of the microprocessor unit, with the signal having a signal level that corresponds to the mean value of the signals of the outputs of the measuring amplifiers; and
the input of the further amplifier is connected to said output of the microprocessor unit.

12. A device in accordance with claim 11, wherein: the microprocessor unit has a further output to which a further signal is sent;
the further signal having the signal level corresponding to the mean value of the signals of the outputs of the measuring amplifiers amplified by a factor; and the further output of the microprocessor unit is connected to the second inputs of the measuring amplifiers.

13. A device in accordance with claim 10, wherein: the summing unit comprises a summing unit amplifier with one input connected to the outputs of the measuring amplifiers such that the signal is sent to an output of the summing unit amplifier with a signal level that corresponds to the mean value of the signals of the outputs of the measuring amplifiers; and
the output of the summing unit amplifier is connected to the second inputs of the measuring amplifiers and to the input of the further amplifier.

* * * * *